US006187546B1

(12) United States Patent
O'Neill et al.

(10) Patent No.: US 6,187,546 B1
(45) Date of Patent: Feb. 13, 2001

(54) METHOD OF ISOLATING CELLS

(76) Inventors: Ian Kenneth O'Neill, 5 Red Hill Close, Great Shelford, Cambridgeshire CB2 5JP (GB); Alexandre Loktionov, 94, Canterbury Street, Cambridge CB4 3QE (GB)

(*) Notice: Under 35 U.S.C. 154(b), the term of this patent shall be extended for 0 days.

(21) Appl. No.: 09/043,010

(22) PCT Filed: Sep. 5, 1996

(86) PCT No.: PCT/GB96/02177
§ 371 Date: Apr. 23, 1998
§ 102(e) Date: Apr. 23, 1998

(87) PCT Pub. No.: WO97/09600
PCT Pub. Date: Mar. 13, 1997

(30) Foreign Application Priority Data

Sep. 6, 1995 (GB) .................................................. 9518156

(51) Int. Cl.⁷ .................................................. G01N 33/533
(52) U.S. Cl. .................... 435/7.1; 435/1.3; 435/7.23; 34/284; 436/174; 436/177; 935/19
(58) Field of Search ........................... 435/7.1, 1.3, 7.23; 34/284; 436/174, 177; 935/19

(56) References Cited

U.S. PATENT DOCUMENTS 4,971,905 * 11/1990 Holmes .

FOREIGN PATENT DOCUMENTS

91/09964 * 7/1991 (WO) .
92/17609 * 10/1992 (WO) .
93/20235 * 10/1993 (WO) .

OTHER PUBLICATIONS

Albaugh et al., Int. J. Cancer, 52:347–350, 1992.*
Biswas et al., J. of Clin. Micro., 32(9):2147–2151, 1994.*
Hardingham et al., Cancer Research, 53:3455–3458, 1993.*
Hedges et al., Proc. of the Society for Exper. Biol. & Med., 157:94–96, 1978.*
Sidransky et al., Science, 256:102–105, 1992.*
Thompson et al., J. Lab. & clin. Med., 73(3):512–520, 1969.*
Dutta, S.K., et al. "Effects of Dietary β–carotine supplementation on nitroso–amine induced squamous cell carcinoma of the esophagus in rats," AGA Abstracts, Supplement to Gastroenterology 108(4):A462 (1995).
Risio, M. et al., "Correlations between Rectal Mucosa Cell Proliferation and the clinical and pathological features of nonfamilial meoplasia of the large intestine," Cancer Res. 51:1917–1921 (Apr. 1, 1991).
Terpstra, O.T. et al., "Abnormal Pattern of cell proliferation in the entire colonic mucosa of patients with colon adenoma or cancer," Gastroenterology 92:704–8 (1987).
Scallmati, A. et al., "Epithelial cell kinetics in the remaining colorectal mucosa after surgery for cancer of the large bowel," Cancer Res. 50:7937–7941 (Dec. 15, 1990).
Al–Sheneber, I.F. et al., "Prognostic significance of proliferating cell nuclear antigen expression in colorectal cancer," Cancer 71:1954–59 (1993).
Iyengar, V. et al., "Human stools as a source of viable colonic epithelial cells," FASEB J. 5:2856–59 (1991).

* cited by examiner

*Primary Examiner*—Long V. Le
*Assistant Examiner*—Bao-Thuy L. Nguyen
(74) *Attorney, Agent, or Firm*—Mathews, Collins, Shepherd & Gould, P.A.

(57) ABSTRACT

The invention provides a method of isolating cells from a faecal stool, the method comprising the steps of a) cooling the stool to a temperature below its gel freezing point, and b) removing cells from the stool whilst maintaining the stool at a temperature below its gel freezing point such that the stool remains substantially intact. The invention further provides methods of purifying cells comprising use of immunomagnetic beads and/or boric acid. Cells isolated according to the invention may be used in diagnostic tests and assay procedures for monitoring a biological or biochemical property of tissue.

21 Claims, No Drawings

METHOD OF ISOLATING CELLS

The present invention relates to a method of isolating cells, especially exfoliated epithelial cells.

Exfoliated epithelial cells consist of cellular components, such as DNA, RNA and proteins, which potentially provide a multiplicity of approaches to identifying and monitoring unhealthy conditions of the epithelium as exemplified by colorectal cancer, polyps and ulcerative colitis. The facile recovery of such cells makes possible the application of a wide variety of test procedures for qualitative and/or quantitative analysis of, for example, DNA alterations, gene expression and enzyme activity.

The early detection of cellular, genetic and other biomarkers of tumorigenesis or malignancy is a critical factor in the prophylaxis and treatment of cancer and other disease conditions. Various cancers including colorectal, lung, oral, pancreatic, bile duct, urinary bladder and some other epithelial tissue cancers occur at substantial incidence (Cancer Incidence in Five Continents, Vol VI, ed. Parkin D. M. et al., IARC Scientific Publications No. 20, IARC, Lyon, France) and have substantial mortality because in many cases tumours are diagnosed too late to be curable due to the absence of non-invasive, inexpensive screening methods for general use. At present many cancer cases are only detected when a tumorous mass or bleeding or other malfunction leads to the use of diagnostic procedures that themselves can only confirm an advanced stage of neoplastic process requiring drastic treatment often with low likelihood of success. Illustrative of this problem is pancreatic cancer in which the early symptoms can be easily confused with those of more common conditions but when the cancer diagnosis is eventually made the average life expectancy is only 3 months. Also illustrative is colorectal cancer which afflicts 5% of the population and kills 3%, but which studies indicate is curable with early intervention. The lack of procedures capable of very early detection of neoplasia at stages before invasion or even before malignancy is evident, although recent methods of detection of cancer-related genetic alterations (Mao L. et al., Cancer Research (Suppl.), 54, 1939s–1940s (1990)) and initial knowledge of a sequence of genetic lesions leading to neoplasia (Fearon E. R. et al., Cell, 67 757–767) provide hope of progress.

Of key importance in the provision of a mass-screening program for early detection and treatment of pre-cancerous and cancerous conditions is the need for simple procedures for obtaining tissue, cell or DNA samples on which diagnostic assays may be performed. For individuals in whom cancer or polyps or a pre-neoplastic lesion has been detected, or are apparently at elevated risk because of genetic predisposition, it is also important to sample the tissue subsequently on a number of occasions to seek evidence of response to treatment or recurrence. Such treatments include those designed to eliminate a tumor, or to induce preventive metabolic changes.

Conventional sampling procedures usually entail taking a tissue biopsy from the patient. However, biopsy procedures are invasive, often require local or general anaesthesia, and at the very least cause considerable discomfort to the patient. Furthermore, except for sampling a tumor or polyp, a biopsy removes a small sample of tissue which is a priori non-representative of the organ or tissue as a whole. Such techniques are therefore unsuitable for routine mass screening.

A screening approach to early detection of colorectal tumors is based on faecal occult blood testing (FOBT). The main advantages of FOBT are its non-invasiveness, simplicity and low cost. However, the presence or absence of blood in stool is not necessarily related to the presence or absence of a tumor. Consequently the method is not free of false-positive results and often fails to detect cancer and especially polyps.

Several studies have indicated that there may be correlation between increased colonocyte proliferation and colorectal cancer risk and/or presence of colorectal tumours (Terpstra O. T. et al., Gastroenterology, 92, 704–708 (1987); Scalmati A. et al., Cancer Res., 50, 7937–7941 (1990); Risio M. et al., Cancer Res., 51, (1991); Al-Sheneber I. F. et al., Cancer, 71, 1954–1959 (1993)). These results, however, often failed to reach statistical significance and were controversial for some patients. The evidence and methods published to date have failed to substantiate increased colonocyte proliferation as providing a basis for a reliable or practical diagnostic test for colorectal cancer risk and/or presence of colorectal tumours.

A method for isolating human cells from homogenised faeces has been reported (Albaugh G. P. et al., *Int. J. Cancer,* 52, 347–350 (1992); Iyengar V. et al., *FASEB J.,* 5, 2856–2859). The reported method employs a homogenised sample of faeces and has been found to be difficult to repeat, and lacks the speed, yields and selectivity to be of use in routine mass screening. Dutta S. K. et al. (AGA Abstracts, *Gastroenterology,* 108, (1995) A463 employed this method based on density gradient separation in an attempt to compare the number of colonocytes recovered per gram of homogenised faecal sample in colorectal cancer patients and control subjects. Although there was a trend toward greater recovery in cancer patients (about twice that of controls), the difference failed to reach statistical significance.

A method for isolating metastatic malignant epithelial cells from blood has also been reported (Hardingham et al. Cancer Research, 53, 3455–3458 (1993)). The method employed immunomagnetic beads labelled with a monoclonal antibody specific for epithelial cells to isolate cells, which were analysed for the presence of a point mutation in the K-ras tumour marker gene using PCR. The direct use of immunomagnetic beads would not, however, be expected to be of general applicability to the isolation of epithelial cells from bodily waste products or gastrointestinal fluids in view of the likelihood of non-specific binding interactions between the immunomagnetic beads and material present in the bodily waste product or gastrointestinal fluid.

Extraction of DNA directly from human stool for detection of cancer-associated gene alterations by diluting small portions of homogenized frozen faeces with a cell lysis solution followed by centrifugation of the resultant suspension and purification with powdered glass has also been reported (Sidransky D. et al., *Science,* 256, 102–105 (1992)). Loktionov and O'Neill (*Int. J. Oncology,* 6, 437–445 (1995)) reported isolation of DNA from rat stool by incubating faeces with cell lysis buffer and a subsequent phenol-chloroform extraction process. In both these cases only limited amounts of pure DNA for PCR amplification were obtained.

There remains therefore a need for methods of cell sampling which (a) are non-invasive or minimally invasive, (b) are quick so as to recover intact cells, (c) provide a large enough quantity of cells suitable for multiple assays, (d) are selective so as to leave behind irrelevant material that may dilute sample or interfere in assays, (e) are capable of providing a representative collection of cells. A further requirement that underlies many assay methods is that actual cells are obtained rather than a simple recovery of DNA or another cellular component present in the cells of interest.

According to the present invention there is provided a method of isolating cells from a faecal stool the method comprising the step of cooling the stool to a temperature below its gel freezing point and removing cells from the stool whilst maintaining the stool at a temperature below its gel freezing point, such that the stool remains substantially intact.

The present invention is applicable to the isolation of mammalian cells from the stool of any animal (for example humans) with particular application to the removal of cells from the surface of the stool. Humans generally produce soft stools compared to the pelleted stools of some animals, such as rodents. It has been found that cooling the stool to a temperature below its gel freezing point stabilizes the structure of the stool so as to permit selective removal of human cells, especially from the surface of the stool. At or below its gel freezing point the stool is converted from a soft to a relatively hard material that retains its shape and can be manipulated. The precise temperature of gel formation varies from stool to stool and is influenced by factors such as diet. The form of stools has been characterised by Degan and Phillips (Gut, (1996), 39, 109–113) on a scale of 7 (watery, no solids) to 1 (separate, hard lumps); the effect of cooling a stool to below its gel freezing point is to convert the stool form from the usual range between 6 (fluffy pieces, ragged edges, "mushy") and 2 (sausage shaped and lumpy) to 1 (separate hard lumps).

Preferably, the stool is maintained at a temperature below its gel freezing point throughout the removal of cells from the stool. It has also been found that the surface layers of the intact stool provide a particularly rich source of exfoliated cells.

The present invention provides a method of isolating a population of epithelial cells which is directly representative of cells in vivo and on which both quantitative and qualitative analysis of cancer-associated phenomena can be performed. A wide range of cancer-associated phenomena are known in principle to occur in tissue and its constituent cells and cell components undergoing the multiple steps of neoplastic transformation, and the present invention provides a non-invasive access to these cells and sub-cellular components thereby permitting the monitoring of many phenomena important in cancer detection, treatment and prevention.

Preferably, the present invention comprises removal of cells from the surface of the stool. The surface layers of the stool provide a particularly rich source of exfoliated cells suitable for isolation. Typically, between one-sixth and one third of colonic epithelial cells are exfoliated per day. Without prejudice to the present invention, it is believed that some of these exfoliated cells may be envisaged as forming a "sheath" around the stool, containing a low proportion of bacterial cells and other faecal matter. It is further believed that the viability of the cells in the surface layers of the stool is facilitated by i) a tendency for the cells to agglomerate into plaques, ii) the availability of oxygen at the surface of the stool and iii) their unique ability to utilize as fuel the butyrate formed locally in high concentrations by microfloral fermentation. Oxidation of butyrate is believed to provide fuel for the cells in the absence of blood-borne nourishment following exfoliation. It has been found that isolation of cells from the surface layers of the stool provides significant advantages in yield, purity and ease of recovery over isolation of cells from homogenized stool.

As used herein the term "surface layers" refers to the layer of faecal material within 1.0 mm, preferably, 0.25 mm, of the surface of the stool.

The method of the present invention may be applied to the stool of any animal, preferably mammal, more preferably human.

Cells may be selectively removed from the cooled and gelled stool by scraping (for example, with a knife or scalpel), dabbing (for example, with a glass slide to provide a "smear" for histological analysis), brushing, blotting or other physical abrasion, or by washing. Preferably cells are selectively removed from the stool whilst maintaining the structure of the stool substantially intact. Preferably the cells are removed from the stool by washing.

It is a particular feature of the present invention that exfoliated cells may be isolated from a stool by a method comprising the steps of:

a) cooling the stool to a temperature below its gel freezing point; and b) washing cells from the surface of the stool with an aqueous solution, whilst maintaining the stool at a temperature below its gel freezing point, such that the stool remains substantially in tact.

It has been found that when a stool above its gel freezing point is washed with a small amount of an aqueous solution, water is quickly absorbed by the stool and no washings obtained. Alternatively, if an excess of aqueous solution is added, the stool absorbs water and forms a slurry or suspension of faecal material. Isolation of exfoliated cells from such a slurry or suspension has proved impractical because of difficulties in separating such cells from large amounts of mucus, bacterial and food waste material present in the stool.

In the present invention the step of cooling the stool to a temperature of below its gel freezing point has the effect of stablizing the structure of the stool. Preferably the stool is cooled to a temperature of −80° C. to 15° C., preferably −10° C. to 15° C., preferably −10° C. to 10° C., more preferably 0° C. to 5° C. It will be appreciated that in order to maintain the stool at a temperature below its gel freezing point, the stool may be washed with an aqueous solution pre-cooled to a temperature below the gel freezing point. Preferably, the aqueous solution is ice-cold. The stool may be cooled to substantially below (eg −20° C. to −80° C.) the gel freezing point for storage prior to isolation of cells. External cooling may be applied to the stool and solution during washing in order to maintain the temperature below the gel freezing point. It has been found that when the cooled stool is washed with an aqueous solution, no significant absorption (typically less than 10%) of water takes place. Furthermore, when the aqueous washings are separated from the stool, by for example decanting or filtering, the washings contain a high concentration of exfoliated cells and greatly reduced contamination by bacterial or food waste materials present in the stool.

The stool may be washed with the aqueous solution one or more times and the washings combined. The washing procedure may also employ gentle agitation. Excessive washing and/or agitation should be avoided so as to avoid significant break-up of the stool or excessive erosion of the surface layer that is rich in exfoliated cells. Preferably the stool remains substantially intact during the washing procedure. Typically, the washings obtained by the procedure of the invention will be pale yellow. Distinct brown colouration of the washings and/or visible evidence of solid particles in the washings is indicative of the presence of significant contamination by mucus, bacterial or food waste materials arising from excessive washing or agitation of the sample. Preferably, the method of the present invention comprises washing the stool with gentle agitation such that brown colouration of washings is not observed.

Preferably, the stool is washed with an aqueous solution containing a short chain fatty acid or salt thereof, preferably a $C_{1-6}$ fatty acid or salt thereof, preferably a salt of butyric acid, more preferably sodium butyrate. It has been found washing with such an aqueous solution leads to improved recovery of exfoliated cells.

Preferably, the stool is washed with an aqueous suspending solution based on a cell culture medium, preferably an isotonic medium such as minimum essential Eagle's medium MEM. Preferably the aqueous solution further contains one or more of the following components: a mucolytic agent such as N-acetylcysteine; an antibiotic such as penicillin, streptomycin, amphotericin B or gentamycin; an inorganic salt such as sodium bicarbonate; a chelating agent such as EDTA and/or an anti-coagulant such as heparin to prevent blood clotting if there is blood in the stool; a protein, such as heat shocked bovine serum albumin, which is thought to assist in breaking up clumps of cells.

The aqueous washing technique described above provides a sample of exfoliated cells in suspension which, for many assay and diagnostic purposes, is of adequate purity. The suspension is, however, typically still contaminated with mucus, bacterial and food waste materials. The cell suspension may be further purified using one or more of the following techniques:

a) the cell suspension may be centrifuged at a relatively slow speed (for example, 250 g). Such centrifugation results in a pellet containing predominantly the desired exfoliated cells. Bacterial cells and mucus are predominantly retained in the supernatant, which can be decanted from the pellet. The pellet may be resuspended in the suspending solution if desired;

b) the cell suspension may be treated with an excess of boric acid. Preferably, the suspension is treated with powdered boric acid and sufficient is employed such that some remains undissolved. The suspension of cells and boric acid is stirred or shaken for several minutes before allowing the boric acid to settle. The excess boric acid may be removed by decanting or filtering the supernatant. Treatment with boric acid has been found to be advantageous in breaking up and removing mucus from the cell suspension.

c) the cell suspension may be treated with immunomagnetic beads comprising magnetic beads to which are bound antibodies capable of selectively binding to the cells of interest; followed by magnetically recovering the magnetic beads to which the cells are bound. Impurities are left in the aqueous suspension. Preferably an excess of immunomagnetic beads is employed in order to maximize recovery of cells.

It will be appreciated that steps (b) and/or (c) may be carried out by adding boric acid and/or immunomagnetic beads, respectively, to an aqueous suspension of the cells obtained by washing the stool. Alternatively, the aqueous solution used to wash the stool may include excess boric acid and/or the immunomagnetic particles.

It will be appreciated that each of steps (a), (b) and (c) are optional and may be omitted when, for example, the stool remains substantially intact during washing and residual mucus does not interfere with subsequent assay procedures.

According to the present invention there is provided a method of separating exfoliated cells from mucus comprising treatment of an aqueous suspension of cells and mucus with boric acid. Preferably, an excess of boric acid is used. As used herein "excess boric acid" means sufficient such that some boric acid remains undissolved.

According to the present invention there is provided a method of isolating cells from a mammalian bodily waste product or alimentary tract fluid comprising the steps of:

a) mixing the sample of the bodily waste product or alimentary tract fluid with immunomagnetic beads comprising magnetic beads to which are bound antibodies capable of selectively binding to the cells; and b) magnetically recovering the magnetic beads to which the cells are bound.

Contrary to expectation, it has been found that mammalian cells may be isolated from a mammalian bodily waste product or alimentary tract fluid using immunomagnetic beads. The use of antibodies capable of specifically binding to a particular type of cell facilitates isolation of that particular type of cell, for example epithelial cells, lymphocytes or macrophages or abnormal cells, such as tumour cells bearing antigenic markers. Preferably an excess of immunomagnetic beads is employed in order to maximize recovery of cells.

Methods of preparing immunomagnetic beads have been described by Hardingham et al. (Cancer Research, 53, 3455–3458 (1993)). Suitable magnetic beads are commercially available from Dynal (Oslo, Norway). The beads may be coated with any antibody capable of binding to the cells of interest. For example, isolation of epithelial cells may be accomplished using beads coated with an antibody capable of binding epithelial cells, such as antibody Ber-EP4 (commercially available from Dako (Gestrop, Denmark)). Isolation of lymphocytes and macrophages may be accomplished using antibody specific for CD8. Isolation of macrophages may be accomplished using antibody specific for CD14. Isolation of other cell types may be accomplished using an appropriate target cell specific antibody.

The antibodies may be bound to the beads directly (for example, covalently) or indirectly (for example via another antibody). An example of indirect binding is described in Hardingham et al. (Ibid.) in which magnetic beads (Dynabeads M-450) covalently coated with sheep anti-mouse IgG were incubated with Ber-EP4.

The use of immunomagnetic beads may be applied to isolation of cells from any mammalian bodily waste product or alimentary tract fluid. As used herein, the term "alimentary tract fluid" refers to any fluid derived from the alimentary tract of an animal, including saliva, bile and pancreatic, duodenal and intestinal fluids. The term "bodily waste product" refers to any waste product of the animal body including faeces, urine and sputum. For example, faeces may be employed as a source of cells from the intestinal tract, particularly colorectal cells; urine may be employed as a source of urinary bladder and prostate cells; saliva or sputum for buccal mucosal, tracheal, bronchial and pulmonary cells; and pancreatic juice, bile or duodenal fluids for pancreatic and cholangiolar cells. Preferably, urine, duodenal fluids or faeces, more preferably faeces, are employed in the method of the present invention.

The number of beads used is selected according to the purpose. For example, an excess of beads is used to maximize the recovery of epithelial cells when the sample contains a limited number of cells (for example, as in urine), and also for the purpose of quantitation when a high ratio of beads to cells ensures maximum cell recovery within the range of cell abundance that is of clinical interest (as with DNA quantification from stool surface). A fixed number of about $3 \times 10^7$ beads has been found convenient for most applications.

The techniques of the present invention as described above may be employed to isolate cells of any type. Such cells include epithelial cells, lymphocytes and macrophages. Preferably, the cells comprise epithelial cells. Epithelial tissues are in general at the highest risk of cancer in the human body. This is probably because of (a) the barrier function of the epithelia leading to exposure to genotoxic agents as a result of dietary and/or tobacco and/or sexual habits and/or occupational exposure, and (b) the high rates of proliferation which serve also to convert some DNA damage into mutations that upset cell cycle control DNA repair and apoptosis mechanisms. As used herein, the term "epithelial cells" includes other cell types that are harboured extensively in the epithelia and which themselves undergo neoplastic change or may be used to reveal the presence of adverse conditions that would potentially result in neoplasia in the epithelia.

According to a further aspect of the present invention there is provided use of a sample of cells obtained according to a method of the present invention in a test or assay for diagnosis or monitoring of a pre-cancerous or cancerous condition. Any conventional histological or immunological assay, test or diagnostic technique may be applied to the cell sample. According to a further aspect of the present invention there is provided use of a sample of cells obtained according to a method of the present invention as a source of DNA for use in a test or assay for the diagnosis or monitoring of a pre-cancerous or cancerous condition.

According to a further aspect of the present invention there is provided a method of isolating DNA from a faecal stool, the method comprising the steps of:

a) Isolating cells from the faecal stool by a method according to the present invention; and b) extracting DNA from the cells.

It has been found that the amount of DNA that can be extracted from exfoliated cells isolated from a stool, and more particularly the "stool DNA index" defined as the weight of DNA isolated divided by the weight of the stool, is an indicator as to whether the subject from whom the stool was obtained has a colorectal neoplastic (cancerous or pre-cancerous) condition.

Thus, according to a further aspect of the present invention there is provided a diagnostic test for colorectal neoplasia in a subject comprising the step of determining the amount of DNA isolatable from a faecal stool obtained from the subject. The diagnostic test of the present invention is performed in vitro.

DNA may be extracted from exfoliated cells isolated from the faecal stool by a method according to the present invention.

Comparison of the amount of DNA isolated, or more preferably the stool DNA index, with values for the amount of DNA isolated or the stool DNA index from faecal stools of subjects known to have colorectal neoplasia (cancerous or precancerous conditions) or are believed to be healthy provides an indication of whether the subject has colorectal cancer, a colorectal precancerous condition or is healthy.

It has been found that when following the protocol described below for isolation of DNA and calculation of stool DNA index, an index of below 600 (generally between 100 and 250 for age <55 years and between 200 and 600 for age >55 years) is typically observed for the stools of healthy subjects, an index in excess of 1400 (generally between 1500 and 6000) is typically observed for the stools of subjects with colorectal cancer, and an intermediate value for this index (between those of healthy persons and those with cancer) is observed for the stools of persons with colorectal polyps befitting the biological intermediacy of polyps in colorectal tumorigenesis (where the stool DNA index is given in nanograms of isolated DNA divided by the weight in grams of the stool).

The significant difference between the stool DNA index for subjects with colorectal neoplasia and healthy subjects provides clear basis for a diagnostic test to distinguish subjects affected by large bowel neoplasia from healthy subjects. Furthermore, the non-invasive nature of the procedure for isolating DNA from the subjects makes the procedure attractive for mass-screening programs. An upward trend in stool DNA index is observed with increasing age of the patient. This, however does not reduce the ability of the technique to identify persons with neoplasia.

It has been demonstrated that the sensitivity and specificity of the protocol for carcinomas both typically exceed 0.90 (90%). In contrast, the conventional faecal occult blood test typically shows sensitivity and specificity in the range 0.4 to 0.7. A further advantage of the present protocol is that it provides a DNA sample that can be used for further analysis or confirmatory tests.

By reason of their general applicability, the methods of isolating cells of the present invention are not limited to the use of cells obtained according to the present invention in the diagnosis of cancer or neoplastic processes but also includes use in an assay for any other adverse process afflicting epithelial tissues wherein examination of exfoliated cells provides information for use in diagnosis, treatment or prevention. These conditions include but are not limited to ulcerative colitis, inflammatory conditions of the relevant epithelia, and incorporation of viral DNA into the genome of some epithelial cells. Cells obtained according to the present invention may also be used in assays to assess beneficial changes, such as within the colorectal epithelium for example deliberately induced metabolic changes by preventative agents. The beneficial changes for which the cells serve as a biomarker include, but are not limited to, alterations to proliferation, to phase I carcinogen-activating enzyme activities and to protective enzymes such as glutathione-s-transferase and NADPH quinone reductase.

Exposure biomarkers have been studied extensively for ascertaining cancer etiology and confirmation of an individual's actual exposure to active components (such as carcinogens, mitogens, promoters) present in an occupation or life-style; the ready extraction of exfoliated epithelial cells provides tissue that is frequently not available or only so with difficulty or in low amounts. Biomarkers of exposure that have been examined include DNA adducts with parts of the carcinogen molecules, oxidative DNA damage, DNA strand breaks and DNA repair enzyme activity. Analysis of some of these biomarkers require the largest practicable sample of DNA since the abundance of adducts is very low. The present invention provides a facile method of isolating exfoliated cells for this purpose.

The relative activities of enzymes that activate carcinogens (phase I) or intercept their reactive metabolites (phase II), have considerable interest for the prevention of cancer and ascertaining the individual's inherited predisposition to cancer. Obtaining epithelial cells for the assay of these enzyme activities is thus of direct interest, as numerous experiments in rodents have shown that anti-cancer action by anti-carcinogens is strongly associated with alteration to these activities, particularly of the phase II enzymes. A typical example (Rao et al (1993), Cancer Res., 53, 2502–2506) showed that oltipraz (a substance related to naturally-occuring compounds in cabbage) reduced the incidence of AOM-induced colorectal tumors in F344 rats to one quarter while increasing the following phase II enzyme activities 2–6 fold in the colonic tissue removed by dissection: (a) overall glutathione S-transferase (hereafter abbreviated as GST) assayed by method of Habig et al (J Biol Chem (1974) 249, 7130–7139): (b) NADP(H): quinone reductase (hereafter abbreviated as QR) assayed by method of Benson et al (Proc Natl AcadSci USA (1980) 77,5216–5220): (c) UDP-glucuronyl transferase assayed by method of Temple et al (J Lab Clin Med (1971) 77, 1015–1019). Many phase II enzymes are known, most of them serving to conjugate the carcinogen with a water-soluble molecule (eg glutathione conjugation by GST). Other enzymes of particular interest and with a similar effect include N-sulphotransferase and N-acetyltransferase (NAT) which sulphate or acetylate a carcinogen, and have an unfortunate effect of further activating a class of carcinogens that are associated with colorectal cancer. A further group of enzymes repair DNA damage. Determining these phase I or II or repair enzyme activities in epithelial tissue is a most active field of cancer research which has practical applications.

Phase I and II enzymes are expressed in human tissues according to both the genetically-determined levels and also those that can be induced by environmental and dietary exposures. Deficiency of certain types of GST enzyme has been associated in many studies in humans with increased risk of colorectal and other cancers, so that deliberate induction of an additional GST activity in the colonic epithelium should help prevent cancer assuming that the rodent results can be extrapolated to humans. Similarly, suppression of phase I enzymes should also be protective. The detection of GST and QR activities in human exfoliated colonic epithelial cells is described herein, faciliated by the present invention of a method to isolate these cells from faeces.

According to the present invention there is provided a method of estimating the enzyme activity or gene expression of epithelial cells comprising isolating exfoliated epithelial cells by a method of the present invention and assaying the cells for enzyme activity or isolating RNA and assaying for gene expression. The invention further provides a non-invasive method for monitoring a biological or biochemical property of epithelial tissue comprising the steps of isolating epithelial cells according to a method of the present invention and assaying the isolated epithelial cells for the biological or biochemical property.

Genotyping an individual is an increasingly important task in determining genetic predisposition, and exfoliated cells provide sufficient DNA for this purpose. DNA fingerprinting for forensic applications is a further application.

The present invention facilitates provision of a sample of cells, such as exfoliated epithelial cells suitable for assay for indications of genetic, morphological or other abnormalities signalling any one or multiple stages of carcinogenesis, between very early pre-neoplastic and advance tumourigenesis. The present invention facilitates routine mass screening of the population of apparently healthy persons who are at elevated risk of cancer development because of well-known reasons of genetic predisposition and/or risk-enhancing exposures, but also includes the use of these techniques for investigating potentially indicative symptoms without performing an invasive procedure. For example, there are identifiable sub-populations such as all males of 50-plus years of age for whom colorectal screening is recommended in some countries but not others due to high cost of the conventional colonoscopy (Hart A. R. et al., Gut, 36, 590–598 (1995)). Other sub-populations exemplified below are also at substantially higher risk and should benefit from early screening;

i) Genetic GST 1 nulled persons—all sites (Idle J. R., Mutat. Res., 247, 259–266 (1991)), ii) GST 1 null and fast oxidator and/or acetylator—colorectal sites (Kadlubar F. F. et al., Env. health Persp., 98, 69–74 (1992)), iii) GST1 null and slow oxidator and/or acteylator—urinary badder sites (Hein D. W., Biochem. Biophys. Acta, 948, 37–66 (1988)), iv) Smokers—lung, pancreas and bladder (US Dept. Health Human Services Publication No. 82-50179 (1982)), v) persons with one or more near relatives with colorectal cancer or polyps—colorectal sites (Utsunomiya J. et al., eds., Hereditary Colorectal Cancer, Tokyo Springer-Verlag (1990)), vi) persons with one or more relatives with gallbladder or pancreatic cancer—gallbladder and pancreatic site (Fernandez et al., Can. Epi. Brom. & Prev., 3, 209–212 (1994)), vii) persons with occupational exposure to aromatic amines—bladder sites Chernozemsky I. N. et al., Environmental Carcinogens; Selected Methods of Analysis Vol 4 IARC Scientific Publications No. 40 eds. Fishbein et al., IARC, Lyon, 3–12 (1981)), viii) persons with occupational exposure to air-borne carcinogens especially polycyclic aromatic hydrocarbons, radon, environmental tobacco smoke, cooking aerosols, wood dust, formaldehyde—lung and sinus/nasal passage sites (IARC Monographs on the Evaluation of Carcinogenic Risks to Humans Col. 1–62 IARC, Lyon), ix) women having many sexual partners and/or with partners having a prior history of many sexual partners—cervical epithelium sites (Bosch F. X. et al., Can. Epi. Brom. & Prev. 3, 375–379 (1984)), Any combination of such genetic predispositions and risk-enhancing environmental exposure as exemplified here places an individual at considerably greater risk of developing cancers of the epithelial tissues and thereby signals the need for repeated screening from an early age such as 35 years.

Furthermore, as chemopreventive procedures (Kelloff et al., Can Epi. Brom. & Prev. 3, 85–98 (1994)) are developed to prevent either the recurrence of dysplasia, polyps or cancer, or of the earlier stages of carcinogenesis prior to these detectable phenomena, screening provides the basis of the essential clinical guidance for selection of which chemopreventive agent is the most individually effective (Szarka et al., in Current Problems in Cancer Ed. R. Ozols 13–16 Mosby-Year Book Inc.). The screening employing the process of the present invention also provides the basis of the subsequent non-invasive routine monitoring to check that the preventive procedures continue in effectiveness. Particularly important in such screening is the assay of cells for enzyme activities, number of cells and morphological characteristics, all of which require intact cells as provided by the present invention.

Furthermore, as more genetic predispositions and lifestyle/familial/occupational risk factors for increased cancer risk are discovered, an increasing number of presently asymptomatic individuals having combinations of such predispositions/factors and thus at very high risk are identified. The methods of the present invention are particularly adapted to facilitate the diagnostic assays and tests, and routine monitoring of such conditions, required by such patients.

A particular advantage of the present invention is that naturally exfoliated cells are sufficiently abundant when collected and isolated by the process of this invention to provide enough cells to afford several assays for the discrimination of indicators of carcinogenesis. The recent availability of methods of detection of early stages of carcinogenesis, for example polymerase chain reaction-based (PCR) assays of mutations in oncogenes associated with tumorigenesis, (Mullis K. B. et al. eds. The Polymerase chain reaction, Birkhauser, Boston) such as K-ras or H-ras (Boson J. L., Cancer Res., 49, 4682–4689 (1989)) or APC (Powell S. M. et al., Nature, 359, 235–237 (1992)) or p53 (Greenblatt et al., Cancer Res., 54, 4855–4878 (1994)), render the present cell isolation process as a basis of inspecting these cells for abnormalities at a convenient time and without the need for a biopsy. The exfoliated cells isolated by the present invention can in principle be used for any type of PCR-based assay. Exfoliated cells isolated by the present invention may also be subjected to existing methods for morphological assay for which cells were not previously available or not available in clean enough state to permit such assays.

A second related advantage is that exfoliation from the whole epithelial surface provides a better sample (except when the location of the tumor is known) than a biopsy which is a priori a non-representative tissue sample. The process of this invention concerns the recovery of the epithelial cells that were at the tissue surface, and the following considerations show that this provides representation of the whole epithelial tissue;

i) the abundance of DNA adducts in epithelial cells at the tissue surface, i.e. easily accessible cells, is quantitively similar to or greater than, and is qualitatively the same as, that in the same tissues from which a biopsy has been also used to remove deeply-located non-surface cells (Stone J. G. et al., Cancer Res., 55, 1267–1270 (1995));

ii) the normal biological processes of epithelial proliferation and growth lead to deeper cells arriving at the surface some time later so that a permanent DNA or other lesion in those cells is cycled to the surface for exfoliation and represents the condition of the underlying tissue. Although a temporary lesion as formed just previously from action of substances in the cavity may affect only the surface cells and have no long-lasting effects by reason that those cells are shortly to be exfoliated, the natural processes of DNA repair (Hanawalt P. C. et al., Mutat. Res., 247, 203–211 (1991)), apoptosis (Hoffman B. et al., oncogene, 9, 1807–1802 (1994)), etc, serve to minimize the continuing existence of all but a very small fraction of genotoxic actions. Although creation of a mutated cell that is not eliminated by apoptosis may arise by either division of stem cells or mutation during cell division at a later stage closer to the tissue surface, this dual origin poses no difference for a genetic assay as to whether the cells were obtained by biopsy or exfoliation.

Thus assay of the exfoliated surface cells as isolated according to the present invention, encompasses the examination of tissues revealing long-term effects as actually already established and also short-term effects as may lead to a long-term effect. Thus by concentrating on the exfoliated cells, the process inherently reflects important features of the whole tissue at risk and does not suffer the scientifically non-representative disadvantages of a local biopsy. Cells isolated according to the present invention are amenable to the wide range of conventional assay procedures employed to characterize diseases and abnormalities in clinical practice. These include staining for pathological and histological study.

DNA recovered from cells obtained according to the present invention may be subject to PCR-based assays for the detection of genetic pre-cancer or cancer indicators. For example, PCR assays for the presence or frequency of mutated Kras, Hras and/or other mutated gene may be conducted.

The invention will now be described with reference to the following examples. It will be appreciated that what follows is by way of example only and that modification of detail may be made without departing from the scope of the invention.

Experimental

A. Isolation of Exfoliated Epithelial Cells from Faeces

The following procedure was performed in a laboratory equipped for handling of faeces and precautions taken to prevent infection, contamination, etc in accord with HSWA and COSHH requirements.

For a typical stool of weight 100 g with dimensions approximately 20 cm length and 2.5 cm diameter and surface area of approx 170 cm², the procedure was as follows:

Ai) the stool sample is excreted directly into a clear plastic stool collection bag 30×40 cm that is held by a device under the toilet seat as in known methods (Bingham et al., Carcinogenesis, 13, 683–690 (1992)), and the bag is then closed with a rubber band immediately;

Aii) the stool and bag are weighed, and the stool weight is found to be usually 40 to 200 g;

Aiii) for convenience and better recoveries, stools should be a minimum of 50 g and in formed shape so that diarrhoea is not desirably present;

Aiv) within a few minutes of excretion, the bag containing the stool is then placed in ice-water with the open end of the bag clipped to the side of the ice-water container so that the hydrostatic pressure excludes air from the bag thus ensuring good thermal contact of the whole stool. The cooling is performed for at least 30 mins;

Av) at this stage, samples can be taken for other purposes in particular to observe cells on the stool surface by touching it lightly with a microscope slide, and for taking portions for other assays (eg for N-nitroso compounds and nitrosating agents (Bingham et al., Gastroenterology, 104, A389 (1993)) that may be interfered with by the following steps of the process. Samples can be taken at this stage as the solidity of the gelled stool minimises exposure of bulk material from its interior;

Avi) 50 ml of an ice cold aqueous suspending solution pH7.4 comprising minimum essential Eagle's medium (MEM) containing phenol red dye (supplied by Sigma) and further containing the following substances is added to the stool and then the bag agitated gently for 5 mins in ice water so as to wash the stool surface—

N-acetylcysteine 50 mM,
3 mM sodium butyrate,
antibiotics: penicillin (500 units/L), streptomycin sulphate (500 mg/L), amphotericin B (1.25 mg/L), gentamycin (50 mg/L),
sodium bicarbonate 1 g/L,
and heat shocked bovine serum albumin 10 g/L.

If the suspending solution is to be stored it may be made up as indicated but omitting the N-acetylcysteine (which may oxidise on storage). On the day of use 0.1 volumes of 50 mM N-acetylcysteine are added to 1.0 volumes of the stored solution. The resulting solution, in which the concentration of components is 9% lower than in the standard suspending solution may be used in place of the standard suspending solution.

The solution is originally a bright pink colour due to the phenol red dye and generally the stool washings are a pink-yellow colour. The agitation is gentle so as not to cause a break up of the stool, break up being signalled by an immediate darkening and brown colouration of the washing;

Avii) The washings containing the suspension of cells is decanted from the bag through a 250 μm sieve on top of a 125 μm sieve supported on top of a large container. 5 g ice and 20 g finely divided boric acid is added to the sieved washings. The stool is washed a second time in the same way. These washings are decanted and passed through the sieves and combined with the first washings.

Aviii) This procedure uses 1 ml of solution per gram of stool, but more cells can be extracted with further washing up to at least 2 ml per gram. Washing with a larger net volume or number of times produces more material, and the precise volumes can be adjusted to suit the stool size and purpose; the washings are swirled within the container to enhance contact with the undissolved boric acid, which is allowed to settle and the supernatant washings decanted. The washings are changed in colour from pink-yellow to yellow by the partial dissolution of the boric acid which causes the pH to change;

Aix) The washings are centrifuged at 250 g for 10 min at 0° C. preferably in 50 ml transparent, graduated plastic tubes with conical bottoms (eg Falcon tubes);

Ax) Then the supernatants are discarded carefully so as to not lose the top part of the pellets. The pellets are generally of volume 1 to 2 ml per 50 ml washings and appear to be dark brown at the lower part (probably fibre and associated cells) and lighter colour at the top;

Axi) Each pellet is resuspended in one 5 ml aliquot of the ice cold suspending solution using gentle passage up and down a coarse Pastette type disposable tube, and then the resuspended pellets combined and diluted with further suspending solution in one of the 50 ml tubes (eg 25 ml total volume is convenient);

Axii) Boric acid, finely divided in pestle and mortar, is made into a 1:1 w/v slurry with cold suspending solution and 10 ml of this slurry added to the suspended pellets. Then the tube is gently agitated end over end for 5 min before allowing the dense undissolved boric acid to settle as a white or buff coloured pellet.

Axiii) $3 \times 10^7$ BerEP-4 immunomagnetic beads are then immediately added. They may be added in any convenient manner, such as in suspension in phosphate buffered saline (PBS). The mixed suspension of cells, beads and unwanted particles then stirred gently with the tube maintained vertical for 5 min with the tube kept in ice-water. BerEP-4 magnetic beads are available from Dynal or may be prepared from M-450 Dynabeads coated with rat anti-mouse IgGl (available from Dynal-Product No. 110.12) by incubation with Ber-EP4 (a mouse anti-human antibody specific for epithelial cells available from Dako) according to the procedure of Hardingham et al. (Cancer Research, 53, 3455–3458 (1993)).

Axiv) The tube containing the mixture of resuspended pellet and beads is gently stirred by rotation and rocking of the container for 10 min on a device such as Dynal MX-1. Magnetic isolation of the cell-bead complex is performed with a magnetic device such a Dynal MPC-1 wherein a very strong magnet is held against the side of the vertical tube and the cell-bead complexes form a brown stripe on the tube side; the undissolved boric acid falls to the bottom of the tube.

Axv) Suction is applied through a broad tube with tapered end so as to suck first the pellet of boric acid and then the supernatant, containing residual bacterial and food waste material, from the tube leaving the brown cell-bead stripe retained magnetically on the tube side.

Axvi) The magnet is removed and 25 ml more suspending solution is used to resuspend the cell-bead complexes. The cell-bead complexes are washed by gently stirring with rotation and rocking for 2 minutes before repeating the magnetic isolation. The supernatant is discarded and the washing repeated, after which the discarded supernatant should be the same bright pink as the original washing solution. A brown colour indicates that irrelevant faecal material had been removed from the stool during its washing, is still contaminating the cells, and that the final wash steps (stage xvii) will need to be repeated several times.

Axvii) The washing of the cell-bead complex is repeated with two further aliquots of the suspending solution (15 ml), the last of which should be the unaltered bright pink colour after the cell-bead complexes have been retained magnetically.

Axviii) Typically the cell-bead complexes are then resuspended again in a minimum volume of any appropriate medium and divided into aliquots in Eppendorf tubes.

B. Isolation of Exfoliated Epithelial Cells from Beneath the Surface of a Stool

In order to extract any sub-surface mammalian cells, the procedure above is adapted as follows:

Bi) an ice-cold stool is first washed thoroughly as in stage vi above using 4 washes each of 0.5 ml per gram of stool. These washes are set aside, and then a portion of the stool typically 10–20 g is placed with 50 g ice in a large plastic stomacher bag 30×40 cm.

Bii) ice-cold suspending solution as above is added, typically 6 ml per gram of faeces.

Biii) The bag is placed in a stomacher machine (eg Colworth stomacher 3500), and stomached for a minimum time eg 15 secs. The bag is removed and the sample allowed to settle for a short time and then checked to see that the stool is broken to small pieces in the millimeter size range without complete homogenisation which results in a permanent brown solution/suspension.

Biv) the whole contents of the bag are then decanted and filtered through a 500 μm sieve on top of a 250 μm sieve on top of a 125 μm sieve supported on a container as above. 5 g of ice are added and then the suspension centrifuged as in stage Aix above.

Bv) the above procedure stages Ax to Axvii is followed.

C. Procedure for Isolation of Exfoliated Epithelial Cells for Quantative Analysis of Total DNA Present The following procedure was used for collection of exfoliated epithelial cells from stools for quantitative analysis of total DNA present. The procedure, which is an abbreviated adaption of the procedure set out in section A above (in particular, omitting treatment with boric acid), may also be employed for collection of cells intended for other assays in which the presence of mucus does not matter.

Ci) steps Ai) to Av) above;

Cii) For a stool weight of at least 30 g, 0.5 ml of the ice-cold suspending solution defined in Avi) above per gram weight of stool is added to the bag containing the stool and the bag gently agitated for 5 minutes in ice water so as to wash the stool surface. For a stool weight of 10 g to 30 g, 15 ml of the ice-cold suspending solution is used;

Ciii) the aqueous suspending solution is decanted from the bag and the washing step repeated;

Civ) the combined decanted washings are then passed through a 250 μm sieve followed by a 125 μm sieve;

Cv) the filtrate is then transferred to 50 ml transparent tubes and examined for colour:

if red or red-yellow and thus relatively un-contaminated, the washings are treated directly with the Ber EP-4 immunomagnetic beads (total 3×10$^7$ as in step Axiii);

if distinctly contaminated (brown colour of fecal material is dominant), then the washings are centrifuged as in step Aix), pellets collected and re-suspended as in steps Ax) and Axi) before proceeding to addition of immunomagnetic beads (total 3×10$^7$) as in step Axiii).

Cvi Steps Axiv) to Axvii) are followed as before.

D. Extraction of DNA from Cell Isolated rrom Faeces

Cell-bead complex obtained according to steps Ci) to Cvi) above were resuspended in 120 μl* of cell lysis buffer (400 mM TrisHCl; pH 8.0; 60 mM EDTA; 150 mM NaCl; 1% SDS).

Di. Add 80 μl of 5% Hexadecyltrimethylammonium bromide (CTAB, final concentration—2%)** and mix well.

Dii. Incubate at 70° C. for 10 min.

Diii. Add 20 μl of proteinase K (20 mg/ml solution) and 200 μl of Buffer AL (QIAamp Blood Kit, QIAGEN) and mix well.

Div. Incubate at 70° C. for at least 30 min.

Dv. Centrifuge at at least 5000 g for 1 min***.

Dvi. Transfer supernatant to a clean tube***.

Dvii. Add 210 μl of isopropanol and mix well.

Dviii. Apply the sample to a QIAamp spin column and centrifuge at at least 5000 g for 1 min. Discard the filtrate.

Dix. Wash the column with 500 μl of Buffer AW (Spin at at least 5000 g for 1 min). Discard the filtrate.

Dx. Repeat step ix). Centrifugation time—3 min.

Dxi. Elute the DNA with sterile water (150 μl) preheated to 70° C. and centrifuge at at least 5000 g for 1 min.

Notes

\* In some cases more lysis buffer is needed to efficiently resuspend exfoliated cells since samples very rich in exfoliated cells are common, especially among cancer patients. Once the cells are resuspended take 120 μl of the suspension for further extraction and make corrections for the change of volume when determining overall DNA amount in the sample.

\*\* This step eliminates some PCR-inhibiting components of faecal mucus which are otherwise co-purified with DNA.

\*\*\*These steps may be repeated.

E. Assay of DNA Yield from Exfoliated Cells

Determine DNA concentration in the sample by measuring UV absorbtion value at 260 nm. Before measuring, the sample may be diluted 1:20 with water (e.g. 40 μl DNA solution+760 μl water). Measurements at both 260 nm and 280 nm allow to assess DNA purity (ratio 260/280 being 1.7–1.8 for pure DNA preparations).

After that the overall amount of DNA for the respective stool sample is calculated. Division of this value by the stool weight gives amount of exfoliated cell DNA in ng per gram of stool (Stool DNA Index). Preliminary results show this Index to be below 600 ng/g in healthy people and significantly higher in both polyp and cancer patients, being in the range of 1500–6000 in most cases of colorectal cancer.

The remaining DNA may be used for any kind of molecular analysis (See section F).

Stool samples have been obtained from 24 healthy people (12 of age<55 years; 12 of age>55 years), 12 colorectal cancer patients, 10 cancer patients from whom tumors had been surgically removed, 9 polyp patients and 5 patients from which polyps had been removed. As used herein, the term "polyp" refers to a neoplasia which morphologically is a tumor with a characteristic macroscopic appearance, usually pedunculated. Microscopically, a polyp may be characterised as a benign adenomatous tumor.

TABLE 1

Stool weight, DNA amount per stool and Stool DNA Index.

| No | Status | Stool Weight (g) | DNA amount/stool (ng) | Stool DNA index (ng/g) |
|---|---|---|---|---|
| 01 | cancer | 15 | 46000 | 3067 |
| 03 | cancer | 15* | 34745* | 2443* |
| 04 | cancer | 8 | 115025 | 14378 |

TABLE 1-continued

Stool weight, DNA amount per stool and Stool DNA Index.

| No | Status | Stool Weight (g) | DNA amount/stool (ng) | Stool DNA index (ng/g) |
|---|---|---|---|---|
| 06 | cancer | 91 | 62770 | 690 |
| 07 | cancer | 18 | 84375 | 4687 |
| 08 | cancer | 11 | 60000 | 5455 |
| 09 | cancer | 40 | 65250 | 1631 |
| 11 | cancer | 191 | 643500 | 3369 |
| 12 | cancer | 40 | 59400 | 1485 |
| 13 | cancer | 180 | 763650 | 4242 |
| 14 | cancer | 43 | 32450 | 755 |
| 15 | cancer | 149 | 296800 | 1992 |
| For the above cancer patients, Mean Stool DNA Index ± S.E. = 3672 ± 1057 | | | | |
| 01' | oper. cancer | 44 | 23375 | 531 |
| 02' | oper. cancer | 135 | 15400 | 114 |
| 03' | oper. cancer | 49 | 45937 | 937 |
| 04' | oper. cancer | 28 | 7200 | 257 |
| 06' | oper. cancer | 96 | 101475 | 1057 |
| 07' | oper. cancer | 74 | 25380 | 343 |
| 08' | oper. cancer | 132 | 52890 | 401 |
| 09' | oper. cancer | 35 | 7425 | 212 |
| 10' | oper. cancer | 152 | 80437 | 529 |
| 11' | oper. cancer | 12 | 3300 | 275 |
| For the above Oper. Cancer patients, Mean Stool DNA Index ± S.E. = 466 ± 98 | | | | |
| 21 | polyp | 145 | 77900 | 537 |
| 22 | polyp | 82 | 59400 | 724 |
| 24 | polyp | 67 | 56000 | 836 |
| 26 | polyp | 149 | 94875 | 637 |
| 28 | polyp | 100 | 426937 | 4269 |
| 30 | polyp | 44 | 109200 | 2482 |
| 31 | polyp | 26 | 53900 | 2073 |
| 32 | polyp | 83 | 38363 | 462 |
| 34 | polyp | 28 | 5100 | 182 |
| 36 | polyp | 76 | 17850 | 235 |
| For the above Polyp patients, Mean Stool DNA Index ± S.E. = 1244 ± 414 | | | | |
| 21' | rem. polyp | 111 | 210994 | 1901 |
| 22' | rem. polyp | 49 | 5950 | 121 |
| 24' | rem. polyp | 65 | 70400 | 1083 |
| 26' | rem. polyp | 34 | 26400 | 776 |
| 28' | rem. polyp | 60 | 40600 | 677 |
| For the above Rem. Polyp patients, - Mean for Stool DNA Index ± S.E. = 912 ± 292 | | | | |
| 42 | healthy < 55 | 236 | 15075 | 64 |
| 43 | healthy < 55 | 147 | 27125 | 185 |
| 44 | healthy < 55 | 106* | 10137.5* | 97* |
| 45 | healthy < 55 | 49* | 7170* | 243* |
| 46 | healthy < 55 | 47* | 12133* | 258* |
| 47 | healthy < 55 | 117.7* | 19932* | 156* |
| 48 | healthy < 55 | 113.3* | 20656* | 212* |
| 49 | healthy < 55 | 192* | 34453* | 189* |
| 50 | healthy < 55 | 139.5* | 21510* | 146* |
| 59 | healthy < 55 | 132 | 77242 | 585 |
| 69 | healthy < 55 | 214.5* | 11312* | 53* |
| 70 | healthy < 55 | 265 | 13750 | 52 |
| For the above Healthy persons (age < 55) – Mean Stool DNA Index ± S.E. = 187 ± 42 | | | | |
| 41 | healthy > 55 | 40 | 9900 | 247 |
| 52 | healthy > 55 | 99 | 46000 | 465 |
| 53 | healthy > 55 | 192 | 46200 | 241 |
| 54 | healthy > 55 | 263 | 46667 | 177 |
| 57 | healthy > 55 | 133 | 57333 | 431 |
| 58 | healthy > 55 | 234 | 101333 | 433 |
| 60 | healthy > 55 | 46 | 23512 | 511 |
| 62 | healthy > 55 | 193 | 86000 | 446 |
| 63 | healthy > 55 | 170 | 96800 | 569 |
| 64 | healthy > 55 | 76 | 12133 | 160 |
| 65 | healthy > 55 | 242 | 163041 | 674 |
| 67 | healthy > 55 | 81 | 36000 | 444 |
| For the above Healthy persons (age < 55) - Mean Stool DNA Index ± S.E. = 400 ± 46 | | | | |
| Overall, For the above Healthy persons (combined ages) Mean Stool DNA Index ± S.E. = 304 ± 38 | | | | |

Notes:
*Average values are used when a few stool samples were available from the same person

TABLE 2 t-test results (P-values) of comparison between the groups.

| | Cancer Operation | Polyps | Removed Polyps | Healthy/ age < 55 | Healthy/ age > 55 | Healthy Combined |
|---|---|---|---|---|---|---|
| Cancer | 0.0123* | 0.0608 | — | 0.0033** | 0.0053** | 0.0001*** |
| Cancer Operation | — | 0.0837 | — | 0.0119* | 0.5368 | 0.0541 |
| Polyps | — | — | 0.6103 | 0.0113* | 0.0379* | 0.0012** |
| Removed Polyps | — | — | — | 0.0018** | 0.0188* | 0.0003*** |
| Healthy/ age < 55 | — | — | — | — | 0.0024** | — |

*P < 0.05
**P < 0.01
***P < 0.001

Conclusion

These data show a highly significant difference between Stool DNA Indexes calculated for colorectal tumour (both cancer and polyp) patients compared to healthy people providing a new non-invasive diagnostic test for colorectal tumours. Furthermore the Index appears to be useful as a tool of postoperational monitoring of cancer patients. Stool DNA Index measured in cancer patients after operation is much lower than before intervention, being within normal range in most cases. The test is therefore useful for operation efficiency control and detection of recurrences.

F. Application of DNA Extracted from Exfoliated Cells for Genetic Analyses

DNA isolated from exfoliated cells using procedure described in section D has been successfully used for PCR amplification. The following assays, employing conventional assay procedures were performed:

1. Genotype determination i) genotyping for N-acetyltransferase 1(NAT-1) gene including amplification of 118 bp fragment followed by RFLP(restriction fragment length polymorphism analysis) allowing the distinction of 4 genotype variants.
ii) Genotyping for Glutathione S-transferase-Theta (GST-T) gene:—the simultaneous amplification of 78 bp fragment of GST-Theta gene (present in GST-T-positive subjects and absent in GST-T-null persons) and a control sequence. Both NAT1 and GST-T have genotype variants associated with increased cancer risk.
2. Gene mutation detection K-ras gene mutations were analysed using a highly sensitive PCR-based technique. It has been shown that the method can be easily used with DNA extracted from feces. Substantial levels of mutant K-ras were detected in some DNA samples from both cancer patients and healthy persons.

These examples illustrate that genomic DNA extracted from exfoliated cells obtained from fecal samples using the technique described in the present invention may be used for virtually any type of genetic analysis. Similar approaches may be applied to mitochondrial DNA.

G. Isolation of Exfoliated Epithelial Cells from Urine, Sputum or Saliva and Faeces Exfoliated cells in urine are selectively separated as follows:

i) Urine, preferably the first urine of the day, is collected in a plastic 1 L bottle or jug or other clean container with an opening of at least 12 cm containing sufficient ice to reduce the temperature to less than 5° C.
ii) After swirling the container to lower the temperature of the urine by melting the ice, $3\times10^7$ Ber-EP4 immunomagnetic beads as previously described are added and the container gently rotated for 5–20 min to maintain the beads in supension and to allow beads to bind to the epithelial cells,
iii) a magnetic plate (such as the 6×4 array of Sm-Co magnets from Advanced Magnetics Inc.) covered in a closely fitted plastic bag is inserted into the urine and slowly rotated for 1 min so as to capture the bead-cell complexes,
iv) withdrawal of the plate/bag from the urine, and then the plate from the bag leaves the bead-cells on the bag surface from which they are resuspended with two 10 ml aliquots of the suspending solution in a 50 ml clear plastic tube,
v) the cells attached to the beads are then washed twice with 10 ml aliquots of the suspending solution and then transferred to a storage tube in the minimum volume for subsequent assay.

The collection of epithelial cells was confirmed by isolation of DNA from the bead-cell complexes according to section D above, and amplification of wild-type K-ras.

Exfoliated cells in sputum or saliva or selectively separated as follows:

i) saliva or sputum is collected in a bottle and diluted with an ice-cold isotonic solution containing a mucolytic agent such as the above-mentioned suspending solution. For the purpose of examining the epithelial surfaces of the mouth and gums, eating is avoided for several hours prior to sample collection and then a conventional tooth-brush used to abrade the surfaced of interest. These may include but are not limited to the buccal mucosa or similar regions exposed to chewing tobacco, tobacco or betel quid, or tobacco permeable bags that create a risk of tumourigenesis locally,
ii) For the purposes of examining epithelial cells of the respiratory system as normally are cleared to the mouth either by muco-ciliary clearance or coughing, the mouth is preferably first cleaned by not eating for several hours before rinsing it with water to eliminate epithelial cells of the mouth. The person then coughs sputum into the collecting tube. The procedure is most readily performed on arising in the morning when an abundance of epithelial cells from the respiratory system us naturally present, particularly in those persons whom this procedure is most indicated i.e. smokers or those occupationally-exposed. However the procedure is not limited to these persons and there are a wide range of individuals as exemplified earlier who are at risk of neoplastic and other respiratory diseases,
iii) After ensuring that the saliva or sputum is diluted enough to reduce its viscosity, immunomagnetic Ber-EP4 beads, of suspension are added to the diluted saliva or sputum and clean-up is performed as for urine.

Exfoliated cells in faeces are selectively separated as follows:

i) the stool sample is excreted directly into a clear plastic stool collection bag 30×40 cm that is held by a device under the toilet seat as in known methods and the bag is then closed with a rubber band immediately;
ii) the stool and bag are weighed, and the stool weight is found to be usually 40 to 200 g;
iii) for convenience and better recoveries, stools should be a minimum of 50 g and in formed shape so that diarrhoea is not desirably present;
iv) within a few minutes of excretion, the stool contained in the opened bag is then placed in ice-water so that hydrostatic pressure excludes air from the bag thus ensuring good thermal contact of the whole stool. The cooling is performed for at least 30 mins;
v) 50 ml of the aqueous suspending solution described above containing $4\times10^7$ BerEP-4 magnetic beads as described above are added and the bag gently agitated for 5 minutes, keeping the bag in ice-water;
vi) the suspension is carefully decanted through a 250 $\mu$m sieve into a container with 5 g ice. Step (v) is repeated and the combined washings placed in the MPC-1 magnetic device;
vii) Magnetic isolation of the cell bead complex is performed as previously described. If the suspension contains an excessive amount of irrelevant faecal material, magnetic isolation may be improved by diluting the suspension with the aqueous suspending solution.

Assays of the cells attached to beads are readily performed by conventional histological techniques or by conventional PCR techniques with a prior step of cell lysis by extended initial heating for 5 min at 95° C. or similar temperature in the PCR apparatus so as to release the DNA.

H. Assays of Enzyme Activities in Exfoliated Cells and Detection of Enzyme Proteins Therein i) Exfoliated cells are isolated according to Section A or G above. In order to remove components of the suspending solution and facilitate assays for enzyme activity, the cells attached to the beads are re-suspended in 10 ml of an aqueous solution cooled to 0° C. in a 15 ml transparent tube; the solution may comprise (a) 50 mMTris-HC1 pH8, 1 mM EDTA and 3 mMDTT, or (b) a conventional phophate-buffered saline pH 7.4. After gentle mixing for 30 secs, the cells are collected by magnetic separation as described above or by centrifugation at 250 g for 5 min. The supernatant solution is then removed and discarded.

ii) This washing step is then repeated one or more times. The collected cell-bead complexes are then suspended with three to ten times their volume of the medium (0.3–1.0 ml in an Eppendorf tube) in which they are to be broken.

iii) a) In one method, any isotonic solution suitable for the subsequent enzyme step can be used for example three volumes of one of the buffers in step (i) above, and the suspension then cooled in ice-water. The cells are disrupted with a powerful ultrasonicator fitted with a titanium horn using several 5-second exposures taking care to avoid significant temperature rise, keeping the tube in ice-water throughout.

b) In an alternative method, the cells are suspended in ten volumes of a lysis buffer such as that in Section B above. By repeated passage through a fine pipette tip, the combination of lysis solution and mechanical breakage provides cell breakage without the high power of the ultrasonicator that may fragment some of the beads. [This is particularly preferred for applications wherein iron etc compounds are to be excluded].

iv) The resulting suspension of cell fragments then may be treated with a solution of protease inhibitor, e.g. 1 part of protease inhibitor solution [for example 8 mg/ml polymethyl sulfonyl fluoride or phenylmethyl sulfonyl fluoride in ethanol or dimethylsulfoxide] per 50 parts of suspension. [This is especially important if the cells contain substantial amounts of protease enzyme as do some cells from the intestinal epithelium.]

v) The resulting suspension is then centrifuged under refrigeration at at least 5000 g for 10 min, and the supernatant removed to a fresh tube.

vi) The sample may then be snap-frozen in solid $CO_2$ or liquid nitrogen and stored at −80° until assay.

vii) Assays for the enzyme activity of interest in the supernatant, and also of the protein concentration, are then performed and the results expressed conventionally as units activity per mg protein. These enzyme activities include those of Glutathione S-transferase (GST), Quinone Reductase (QR), Atase, FaPY glycosylase, and in principle can be any enzyme of interest.

viii) Isolated exfoliated cells from feces from seven persons were subjected to this procedure, for assay of total GST (using CDNB substrate) and for QR activities. The results are presented in Table 3 below.

TABLE 3

Results Of Phase II Enzyme And Protein Assays In Exfoliated cells Isolated From Human Faeces

| Donor (sample code) | Protein (mg/ml) | GST (CDNB substrate) ($\mu$mol/min/mg protein) | QR ($\mu$mol/min/mg protein) |
|---|---|---|---|
| A (505) | 6.87 | 0.209 | 0.037 |
| A (506) | 6.65 | 0.145 | 0.035 |
| B (CxC3) | 5.34 | 0.166 | 0.034 |
| C (65CL) | 5.09 | 0.107 | 0.039 |
| D (CXH47) | 0.93 | 0.48 | 0.059 |
| D (CXH47a)* | 1.55 | 0.69 | 0.034 |
| E (CXH48) | 4.9 | 0.20 | 0.018 |
| E (CXH48a)* | 2.67 | 0.39 | 0.032 |
| F (CXH49) | 3.6 | 0.37 | 0.032 |
| F (CXH49a)* | 1.6 | 0.41 | 0.053 |
| G (CXH66) | 0.37 | 2.7 | 0.26 |
| G (CXH66a)* | 0.45 | 2.5 | 0.23 |

*these samples were collected from the same donor 1–2 weeks after collection of the first sample following consumption of a different diet intended to alter phase II enzyme activity.

These results demonstrate that exfoliated cells can be collected and used to monitor representative phase II enzyme activities of intestinal epithelial cells, of importance in cancer prevention due to the established inducibility by anti-cancer agents of these enzymes and their roles in preventing DNA damage.

ix) Assay of the supernatant by gel electrophoresis and means to visualise the separated proteins, e.g. staining with Page Blue or by a Western Blot, provides a method to specifically detect the presence of the enzyme in the exfoliated cells even if no activity is found. This can be of interest for epithelial cells when exposures at the epithelial interface result in enzyme exhaustion (e.g. Atase) or inhibition (e.g. GST). This procedure also provides a check that extraneous protein, e.g. the BSA used in the cell isolation procedure, has been removed.

x) Alternatively, collection of RNA from the supernatant by known procedures, followed by assay of the specific RNA for the enzyme, provides a means to detect expression and induction of the enzyme even if no activity or protein is found.

What is claimed is:

1. A method of isolating cells from a faecal stool, the method comprising the steps of:
    a) cooling the stool to a temperature below its gel freezing point;
    b) removing cells from the stool while maintaining the stool at a temperature below its gel freezing point, such that the stool remains substantially intact.

2. A method according to claim 1 wherein cells are removed from the surface layers of the stool.

3. A method according to claim 2 wherein cells are removed from the surface layers of the stool by scraping, dabbing, brushing, blotting or other physical abrasion.

4. A method according to claim 3 wherein less than 1.0 mm of the surface layers of the stool are removed.

5. A method of isolating cells from a fecal stool comprising the steps of:
    a) cooling the stool to a temperature below its gel freezing point; and
    b) washing cells from the surface of the stool with an aqueous solution, while maintaining the stool at a temperature below its gel freezing point, such that the stool remains substantially in tact.

6. A method according to claim 5 wherein the stool is washed with an aqueous solution containing a short chain fatty acid or salt thereof.

7. A method according to claim 6 wherein the stool is washed with an aqueous solution containing sodium butyrate.

8. A method according to claim 1 wherein the stool is cooled to a temperature of −10° C. to 10° C.

9. A method according to claim 8 wherein the stool is cooled to a temperature of 0° C. to 5° C.

10. A method according to claim 1 further comprising the steps of:
   c) mixing an aqueous suspension of the cells obtained with immunomagenetic beads comprising magnetic beads to which are bound antibodies which selectively binds to the cells; and
   d) magnetically recovering the magnetic beads to which the cells are bound.

11. A method of isolating DNA from the faecal stool, the method comprising the steps of:
   a) isolating cells from the faecal stool by the method of claim 1; and
   b) extracting the DNA from the cells.

12. The method of claim 11, further comprising the step of purifying the suspension of cells by one or more methods selected from (a) centrifuging, (b) treatment with excess boric acid, and (c) (i) treatment with immunomagnetic beads comprising magnetic beads to which are bound antibodies which selectively binds to the cells and (ii) magnetically recovering the magnetic beads to which the cells are bound.

13. A method of estimating the enzyme activity or gene expression of epithelial cells comprising the steps of: isolating cells according to the method of claim 1 and assaying the cells for enzyme activity or isolating RNA and assaying for gene expression.

14. A method of isolating cells comprising the steps of:
   a) providing a suspension of cells in aqueous solution according to claim 5;
   b) mixing the suspension of cells with immunomagnetic beads comprising magnetic beads to which are bound antibodies which selectively binds to the cells desired to be isolated; and
   c) magnetically recovering the magnetic beads to which the cells are bound.

15. A method according to claim 14 wherein the antibodies comprise Ber-EP4 antibodies which bind to epithelial cells.

16. A method according to claim 14 wherein the cells are human cells.

17. A method according to claim 14 wherein the cells comprise exfoliated epithelial cells.

18. A method of isolating cells from a faecal stool, the method comprising the steps of:
   a) cooling the stool to a temperature below its gel freezing point in the range −80° C. to 15° C.; and
   b) washing cells from the surface layers of the stool with an aqueous solution while maintaining the stool at a temperature below its gel freezing point such that the stool remains substantially intact, wherein the aqueous solution contains a fatty acid having from one to six carbon atoms or a salt thereof, thereby providing an aqueous suspension of cells.

19. A method of detecting or monitoring at least one biological or biochemical property of epithelial tissue of a human subject comprising the steps of: isolating cells from the subject using the method of claim 1 and assaying the isolated cells for the biological or biochemical property.

20. The method of claim 19 in which the step of assaying the isolated cells comprises assaying the cells for enzyme activity.

21. The method of claim 19, wherein the step for assaying the isolated cells comprises isolating RNA and assaying for gene expression.

* * * * *